United States Patent [19]
Wilk

[11] Patent Number: 6,139,499
[45] Date of Patent: Oct. 31, 2000

[54] ULTRASONIC MEDICAL SYSTEM AND ASSOCIATED METHOD

[76] Inventor: Peter J. Wilk, 185 West End Ave., New York, N.Y. 10023

[21] Appl. No.: 09/253,593

[22] Filed: Feb. 22, 1999

[51] Int. Cl.$^7$ .................................................. A61B 8/00
[52] U.S. Cl. .......................................... 600/443; 128/916
[58] Field of Search .................................. 600/407, 427, 600/442, 443, 447; 128/916; 382/128

[56] References Cited

U.S. PATENT DOCUMENTS

| | | |
|---|---|---|
| 3,552,382 | 1/1971 | Mount . |
| 3,927,662 | 12/1975 | Ziedonis . |
| 4,048,616 | 9/1977 | Hart et al. . |
| 4,315,514 | 2/1982 | Drewes et al. . |
| 4,623,219 | 11/1986 | Trias . |
| 4,646,158 | 2/1987 | Ohno et al. . |
| 4,757,820 | 7/1988 | Itoh . |
| 4,991,604 | 2/1991 | Wurster et al. . |
| 5,078,143 | 1/1992 | Okazaki et al. . |
| 5,091,893 | 2/1992 | Smith et al. . |
| 5,099,459 | 3/1992 | Smith . |
| 5,135,001 | 8/1992 | Sinofsky et al. . |
| 5,163,436 | 11/1992 | Saitoh et al. . |
| 5,167,231 | 12/1992 | Matsui . |
| 5,203,336 | 4/1993 | Iida et al. . |
| 5,394,877 | 3/1995 | Orr et al. . |
| 5,417,215 | 5/1995 | Evans et al. ............................ 600/442 |
| 5,435,311 | 7/1995 | Umemura et al. . |
| 5,437,278 | 8/1995 | Wilk . |
| 5,448,994 | 9/1995 | Iinuma . |
| 5,488,952 | 2/1996 | Schoolman . |
| 5,494,041 | 2/1996 | Wilk ........................................ 600/427 |
| 5,497,776 | 3/1996 | Yamazahi et al. ...................... 600/445 |
| 5,555,512 | 9/1996 | Imai et al. .............................. 364/550 |
| 5,570,430 | 10/1996 | Sheehon et al. ........................ 382/128 |
| 5,611,343 | 3/1997 | Wilson . |
| 5,611,345 | 3/1997 | Hibbeln . |
| 5,619,999 | 4/1997 | Von Behren et al. . |
| 5,666,953 | 9/1997 | Wilk . |
| 5,682,895 | 11/1997 | Ishiguro ................................. 128/916 |
| 5,734,739 | 3/1998 | Sheehon et al. ........................ 382/128 |
| 5,806,521 | 9/1998 | Morimoto et al. ..................... 600/427 |
| 5,817,019 | 10/1998 | Kawashima ............................ 168/916 |
| 6,007,489 | 12/1999 | Yost et al. .............................. 600/449 |

*Primary Examiner*—Franics J. Jaworski
*Attorney, Agent, or Firm*—R. Neil Sudol; Henry D. Coleman

[57] ABSTRACT

A medical apparatus includes an ultrasonic probe having an ultrasonic wave emitter and an ultrasonic wave sensor. The probe is movable along a skin surface of a patient in pressure-wave transmitting contact with that skin surface. An ultrasonic frequency generator is operatively connected to the wave emitter, while an ultrasonic-wave preprocessor is operatively connected to the sensor for periodically processing reflected ultrasonic pressure waves detected by the sensor. The wave preprocessor is programmed to derive preliminary structural data pertaining to the internal tissues of the patient, where the data consists essentially of separate sets of data, each set corresponding to a respective location of the probe relative to the patient. A memory is operatively connected to the preprocessor for storing the sets of data. A main processor is in turn operatively connected to the memory and/or the preprocessor for analyzing the preliminary structural data of the stored sets of data to determine three-dimensional shapes of the internal tissues of the patient. The main processor includes or is connected to a video signal generator which produces a video signal encoding a relatively high-resolution video image of the three-dimensional shapes. This video signal generator is connected to a video monitor for displaying the video image.

20 Claims, 1 Drawing Sheet

ULTRASONIC MEDICAL SYSTEM AND ASSOCIATED METHOD

BACKGROUND OF THE INVENTION

This invention relates to an ultrasonic medical system. More particularly, this invention relates to a medical system which determines three-dimensional shapes of internal organs by using ultrasonic pressure waves. This invention also relates to a method useful in medical diagnosis and treatment.

In recent years, the escalation of medical costs has captured substantial media and regulatory attention. One reason for the escalating costs is the ever increasing use of expensive machines and testing techniques. Computed assisted tomography (CAT scanning), magnetic resonance imaging (MRI) and some radiological techniques have been in the forefront of contributing to mounting medical costs. In addition to being expensive, these devices are heavy and bulky, making them ill suited to transport.

One type of medical scanning device which is less expensive to manufacture, use, and maintain than CAT scanners and MRI scanners is an ultrasonic scanner. Ultrasound is commonly used in monitoring the development of fetuses in utero. Disadvantages of ultrasound are chiefly derived from the low quality of the images produced. These images are not optical quality images and require substantial training to interpret. Even personnel of substantial experience can misread an ultrasound image, with the erroneous or inaccurate results leading to patient trauma and worse.

In conventional ultrasound scanners, image information is entered into long-term memory only at the specific command of the operator. Upon seeing an image on a video monitor which provides apparently useful information, the operator actuates an input device which induces storage of the image displayed at that instant on the video monitor.

OBJECTS OF THE INVENTION

An object of the present invention is to provide an alternative to conventional medical imaging systems.

A further object of the present invention is to provide a medical imaging system which exhibits reduced costs over conventional imaging systems such as CAT scanners and MRI machines.

A particular object of the present invention is to provide a medical imaging system which can be used during the performance of so-called minimally invasive medical operations.

It is an additional object of the present invention to provide a medical imaging system which is portable.

Another object of the present invention is to provide a medical operating method which provides real time imaging in a cost effective manner.

These and other objects of the present invention will be apparent from the drawings and descriptions herein.

SUMMARY OF THE INVENTION

A medical method utilizes, in accordance with the present invention, an ultrasonic probe having transmission and reception capabilities. The probe is moved over a skin surface of a patient, while the probe is maintained in pressure-wave-transmitting contact with that skin surface. During the moving of the probe, an outgoing ultrasonic pressure wave is transmitted from the probe into the patient. Substantially simultaneously therewith, reflected ultrasonic pressure waves are received from internal tissues of the patient and detected by the probe. The received reflected ultrasonic pressure waves are periodically preprocessed to derive preliminary structural data pertaining to the internal tissues of the patient. This preliminary structural data consists essentially of separate sets of data, each of the sets of data corresponding to a respective location of the probe relative to the patient. Thus, as the probe is moved along the skin surface of the patient, data is collected and processed at a multiplicity of spaced points along the path of movement of the probe. Each set of data is essentially equivalent to a conventional ultrasound image and has the resolution and information content thereof. These sequential sets of data are stored and analyzed to determine three-dimensional shapes of the internal tissues of the patient. From this three-dimensional shape data, a video signal is generated which encodes a relatively high-resolution video image of the three-dimensional shapes. This image may be displayed on a monitor to which the video signal is transmitted. The video image thus produced has a definition and quality approximating an image generated by an optical camera.

The three-dimensional shapes are stored prior to the generation of the video signal. At that juncture, instructions may be provided by an operator, determining such parameters as the angle of view, the depth of penetration, and the degree of magnification of the internal tissue structures provided in the video image. The depth of penetration corresponds to a selection of which tissues and organs the operator desires to view on the monitor. If deeper tissue structures are selected, the overlying tissues arc essentially filtered out by the selection process.

The successive encoded ultrasound images of the patient's internal tissues are generally gathered as quickly as the processing allows. The successive ultrasound image data sets are each generated from a respective set of reflected ultrasonic pressure waves received immediately prior to generation of the respective ultrasound image. If the probe is moved slowly over the skin surface of the patient, the sets of data are derived from closely spaced points. However, it is to be noted that the rate at which the probe is moved during the data gathering process has little effect on the quality of the final image displayed on the monitor. Instead, the length of time of the movement and the extent of the path of probe movement about the tissues of interest contribute more significantly to image resolution and the completeness of the three dimensional shape construction.

The probe is generally a manipulable carrier in the form of a wand having a handle portion and a head portion. The probe is moved by holding the wand by the handle and moving the wand while maintaining the head in contact with the skin of the patient. The head carries at least one electroacoustic transducer for generating the outgoing ultrasonic pressure wave and at least one acoustoelectric transducer for sensing incoming pressure waves which result from reflection of the outgoing wave at various tissue interfaces internal to the patient.

Alternatively, the probe may include a flat carrier such as a flexible web. In any event, where the probe includes a plurality of acoustoelectric sensors, the receiving of the reflected ultrasonic pressure waves from the internal tissues of the patient includes operating the sensors to generate respective electrical signals encoding the ultrasonic pressure waves.

It is contemplated that the probe is moved through manual control of an operator. However, it is possible that in some applications, an automatic movement of the probe over the skin surface of the patient will be advantageous. In that case, the probe is mounted to a robotic arm which is programmed to execute a predetermined path relative to the patient. The mounting of the probe to the robotic arm may be spring loaded to ensure proper pressure-wave-transmitting contact between the probe and the skin surface of the patient. The robotic arm may be further provided with a nozzle for applying a gel to the skin of the patient ahead of the advancing probe to facilitate the transmission of the pressure wave to and from the probe.

A medical apparatus in accordance with the present invention comprises an ultrasonic probe having an ultrasonic wave emitter and an ultrasonic wave sensor. The probe is movable along a skin surface of a patient in pressure-wave transmitting contact with that skin surface. An ultrasonic frequency generator is operatively connected to the wave emitter, while an ultrasonic-wave preprocessor is operatively connected to the sensor for periodically processing reflected ultrasonic pressure waves detected by the sensor. The wave preprocessor is programmed to derive preliminary structural data pertaining to the internal tissues of the patient, where the data consists essentially of separate sets of data, each set corresponding to a respective location of the probe relative to the patient. A memory is operatively connected to the preprocessor for storing the sets of data. A main processor is in turn operatively connected to the memory and/or the preprocessor for analyzing the preliminary structural data of the stored sets of data to determine three-dimensional shapes of the internal tissues of the patient. The main processor includes or is connected to a video signal generator which produces a video signal encoding a relatively high-resolution video image of the three-dimensional shapes. This video signal generator is connected to a video monitor for displaying the video image.

In accordance with another feature of the present invention, the main processor includes processing modules responsive to instructions from an operator for selecting the angle of view of the three dimensional shapes, the depth of penetration or the focal plane of the video image, and the degree of magnification of the internal tissue structures provided in the video image. The operator thus effectively has control over which tissue structures are to be viewed on the monitor, the magnification at which the tissue structures appear, and the angle at which the tissue structures are viewed. These parameters may be simply adjusted by feeding instructions to the main processor and/or the video signal generator via a keyboard, a mouse or other computer input peripheral.

Generally, the preprocessor includes circuitry for generating electrically encoded ultrasound images corresponding to the sets of data are, where each of the images is generated from a respective set of reflected ultrasonic pressure waves received immediately prior to generation of the respective ultrasound image.

The probe may take the form of a wand having a handle portion and a head portion. Alternatively, the probe may have another shape such as a web which may be pulled in different directions over the patient.

Diagnosis is further facilitated by generating an electrical signal encoding the determined three dimensional shapes of the internal organs and wirelessly transmitting the additional signal to a remote location. Thus, consultations with experts are possible from remote locations.

It is to be noted in this regard that an ultrasonic imaging device in accordance with the present invention is essentially as portable as conventional ultrasound equipment and significantly more portable than conventional imaging systems such as CAT scanners and MRI machines. Thus, imaging, diagnosis and treatment is possible even where patients do not have ready access to a hospital facility. The images may be transmitted from remote locations to global medical centers where experts can view the internal structures for diagnosis and therapeutic evaluation.

Another advantage of an ultrasonic imaging device in accordance with the present invention is that the basic steps executed by operating personnel, namely, the moving of a probe over a skin surface of the patient is the same as in conventional ultrasound. Thus, the marketing of the imaging device is facilitated. This ease of use is the result of automatic processing of the gathered ultrasonic information by the processor.

DESCRIPTION OF THE PREFERRED EMBODIMENTS

Figure 1:
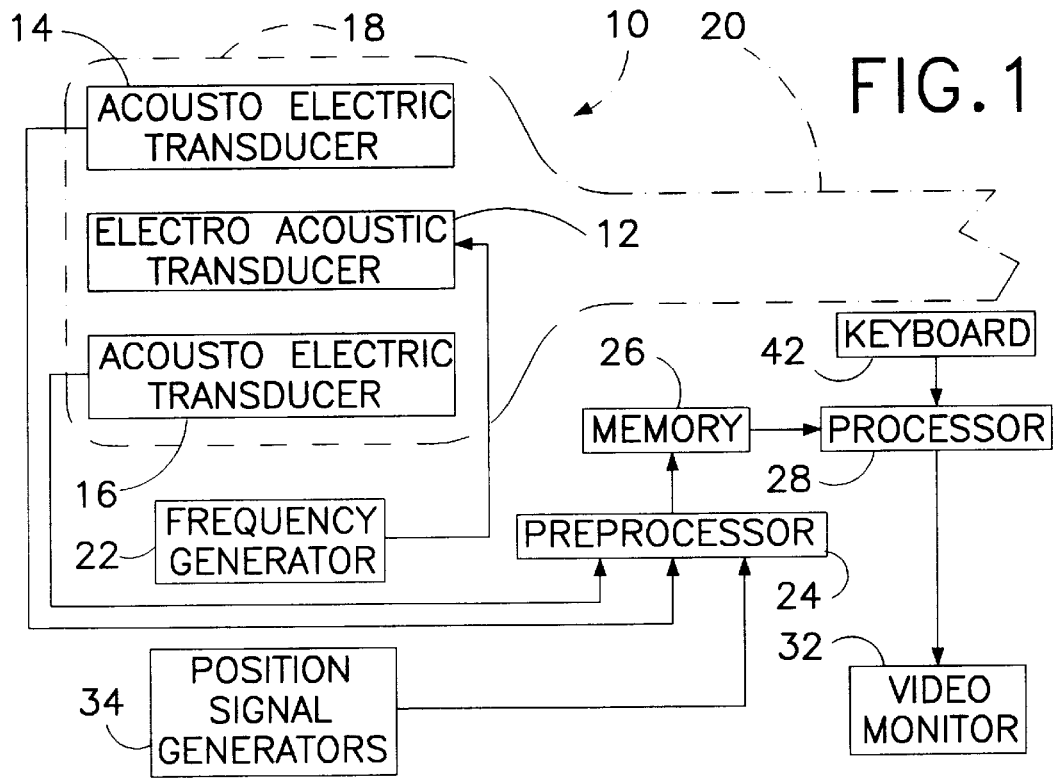
FIG. 1 is a block diagram of a medical apparatus in accordance with the present invention.

As illustrated in FIG. 1, a medical apparatus comprises an ultrasonic probe 10 having an electroacoustic transducer 12 serving as an ultrasonic wave emitter and a plurality of spaced acoustoelectric transducers 14 and 16 serving as ultrasonic wave sensors. Transducers 12, 14, and 16 include piezoelectric crystals which are mounted to a head 18 of probe 10. Head 18 is disposed at the distal end of a handle 20.

Probe 10, and particularly head 18 thereof, is movable along a skin surface of a patient (not shown) in pressure-wave transmitting contact with that skin surface. Generally, it is contemplated that the patient's skin surface is coated with a layer of a gel medium designed to enhance ultrasonic wave transmission between the skin surface and the transducers 12, 14, 16 in head 18 of probe 10. This layer may be applied in a separate step before the placement of the probe in contact wit the patient. Alternatively, probe 10 may be provided with a nozzle (not shown) communicating with a reservoir or pressurized gel for ejecting gel in front of the moving probe head 18.

An ultrasonic frequency generator 22 is operatively connected to electroacoustic transducer 12 for energizing that element with an electrical voltage of a predetermined ultrasonic frequency or a group of discrete ultrasonic frequencies. Alternatively, frequency generator 22 is programmed to produce an electrical voltage having a series of different ultrasonic frequencies.

A preprocessor 24 is operatively connected to acoustoelectric transducers 14 and 16 for periodically processing reflected ultrasonic pressure waves detected by those sensors. As used herein, the word "periodic" or "periodically" refers to a series of successive occurrences. Generally, the processing of ultrasonic pressure waves occurs cyclically at regular intervals, for example, 32 or 64 times per second.

During each processing cycle, preprocessor 24 operates similarly to conventional ultrasonic wave analyzers which generate low-resolution images from an ultrasonic probe. Over several cycles, preprocessor 24 thus produces a series of data sets each encoding information equivalent to a conventional ultrasound image. Generally, although not necessarily, each data set is taken at a respective location of the probe head 18 relative to the patient. These ultrasound-image data sets constitute preliminary structural data pertaining to the internal tissues of the patient and are automatically stored as a matter of course in a memory 26 which is operatively connected to preprocessor 24. This automatic storage of all the ultrasound image data sets during an ultrasound examination differs from conventional ultrasound diagnostic procedures wherein images are stored for subsequent, non-real-time use only in response to a specific user or operator command.

A main processor 28 is operatively connected to memory 26 and/or preprocessor 24 for analyzing the preliminary structural data of the stored sets of data to determine three-dimensional shapes of the internal tissues of the patient. Processor 28 includes or is connected to a video signal generator 30 (FIG. 2) which produces a video signal encoding a high-resolution video image of the three-dimensional internal-tissue shapes. Video signal generator 30 is connected to a video monitor 32 for displaying the video image.

In order to compute three-dimensional surfaces from the essentially two-dimensional data sets in memory 26, it is necessary to supply processor 28 with three-dimensional reference information. This positional reference information is supplied by a plurality of signal generators 34 (FIG. 1) which are generally placed on or near the patient prior to the operation of probe 10 to collect the ultrasound image data. Signal generators 34 may include, for example, respective ultrasonic pressure wave emitters (not separately illustrated) which are placed in contact with the skin surface of the patient at spaced locations. In that case, signal generators 24 further include ultrasonic sensors (not separately illustrated) for detecting pressure waves produced by the wave emitters of the other signal generators 34. The pressure waves produced by the wave emitters of signal generators 34 are preferably of frequencies which are detectably different from the frequency or frequencies produced by generator 22.

It is to be noted that a patient is generally resting on a hard support surface which provides a reflective reference surface for ultrasonic data collection waves. In some cases, it may be desirable to disposed a flexible reflective surface along other surfaces of the patient, for example, along flanking surfaces or even around the entire patient.

The positional reference information provided by signal generators 34 is collated and synthesized by preprocessor 24 and utilized by a surface identifier module 36 and a shape determination module 38 (FIG. 2) of main processor 28 to isolate various tissue surfaces internal to the patient and to connect those surfaces to identify three-dimensional shapes and organ configurations. The identification of three-dimensional tissue structures and organ configurations may be implemented in part by pattern recognition techniques according to which processor 28 compares partially identified surfaces, surface configurations and locations thereof to predetermined average or nominal tissue structures and organ configurations which are stored, for instance, in memory 26. This pattern recognition facilitates the detection, isolation and identification of actual tissue structures and organ configurations in the patient.

Determination module 38 is connected at an output to an image or view selector unit 40 which is connected to a keyboard 42 or other input peripheral via an interface 44. In response to instructions from keyboard 42, selector unit 40 determines a view to be displayed on video monitor 32.

Figure 2:
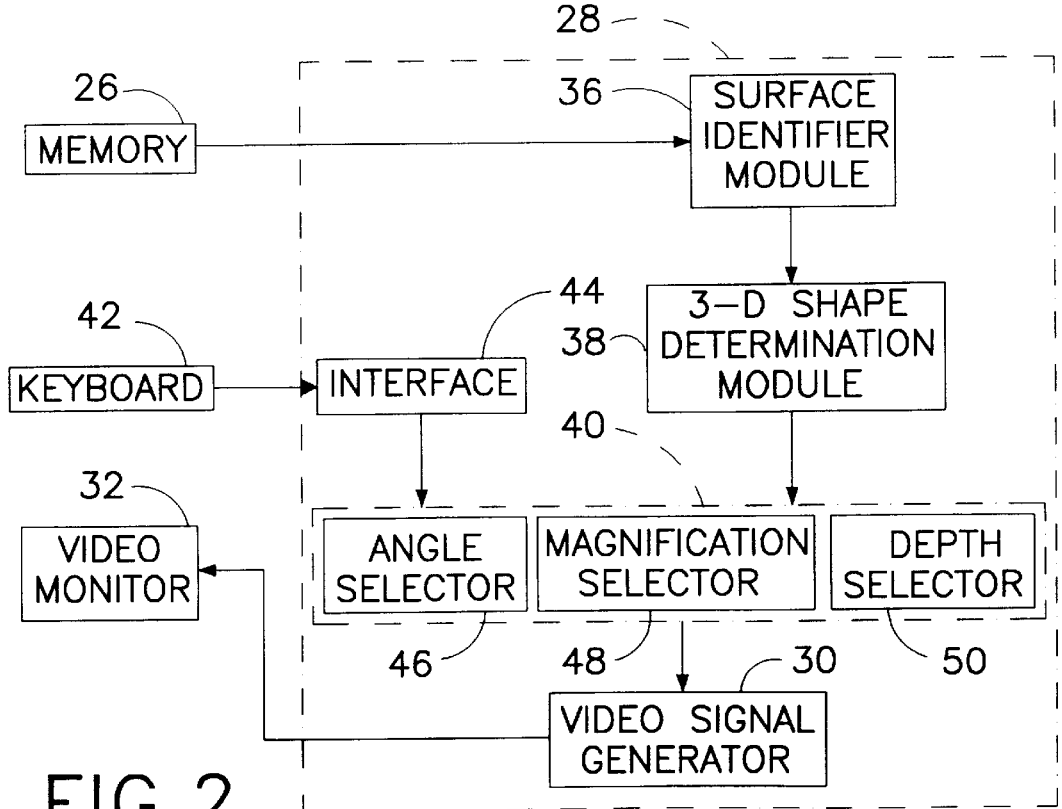
FIG. 2 is a block diagram of a processor shown in FIG. 1, also showing elements periperal to the processor.

As shown in FIG. 2, view selector unit 40 includes an angle selector 46 for determining the angle from which the various internal tissue surfaces and organs are to be viewed on monitor 32. For example, using keyboard 42, an operator may command angle selector 46 to select a left view or alternatively an upper view of an embryo inside a pregnant patient. It is contemplated that the range of view angles selectable by selector 46 is substantially continuous throughout a sphere surrounding the patient.

Selector unit 40 additionally incorporates a magnification selector 48 for choosing the field of view at the view angle determined by angle selector 46. At higher magnifications, the field of view is smaller than at low magnifications. In viewing an embryo, a high magnification will result in viewing an ear alone, while a low magnification shows the entire head and a lower magnification reveals the entire embryo.

View selector 40 also contains a depth selector 50 for determining degree of penetration of the view displayed on monitor 32. A large depth or penetration of an embryo in an advanced state of development will show the heart valves, and a smaller depth will reveal rib surfaces.

In response to incoming ultrasound-image data sets and instructions input by an operator via keyboard 42, view selector 40 generates image data completely specifying an image which may be displayed on monitor 32. This image data is transmitted to video signal generator 30 which produces a video signal incorporating the image data in proper format for display on monitor 32. The video image visible on monitor 32 approaches the quality and resolution typically found in optically generated images, for example, in images generated by charge-coupled devices. To enhance the image quality and resolution, if necessary, various off-the-shelf software may be used.

It is to be understood that the various functional modules of processor 28 are preferably realized as generic digital processing circuits modified by programming to perform the respective specific functions.

Although the invention has been described in terms of particular embodiments and applications, one of ordinary skill in the art, in light of this teaching, can generate additional embodiments and modifications without departing from the spirit of or exceeding the scope of the claimed invention. For example, probe 10 may take a form different from the conventional wand-type depicted schematically in FIG. 1. Such an alternative configuration is a flexible web such as that disclosed in U.S. Pat. Nos. 5,666,953 and 5,871,446 and in allowed U.S. patent application Ser. No. 892,955 filed Jul. 16, 1997, the disclosures of which are hereby incorporated by reference.

In some applications, it may be advantageous to provide for an automatic movement of the probe over the skin surface of the patient. In that case, the probe is mounted to a robotic arm which is indexed along a pre-established path over the skin surface of the patient. In that case, the robotic arm includes a stationary frame which is positioned next to the patient. Alternatively, the probe may be mounted to a small vehicle which is self-propelled to negotiate a path along the skin surface of the patient.

It is to be noted that the use of pattern recognition to identify tissue structures and organ configurations as discussed herein may be used where structural tissue data is obtained by a sensor array on a flexible web or other carrier as disclosed, for example in U.S. Pat. Nos. 5,666,953 and 5,871,446.

In addition, pattern recognition may be used to display identification symbols on video monitor 32 to assist an operator in identifying organs displayed in whole or in part on the monitor. This display of identifying symbols on monitor 32 is particularly useful when only portions of organs and internal tissue structures are displayed on monitor 32, for example, when parts of the organs or tissue structures are deleted in order to show underlying structures. The display of identifying symbols on monitor 32 is discussed in U.S. Pat. No. 5,494,041, the disclosure of which is hereby incorporated by reference.

As discussed in U.S. Pat. No. 5,666,953, the video output of the ultrasonic scanning system disclosed herein may be connected to a telecommunications link for transferring the visually appreciable information to a remote location for inspection by expert diagnosticians.

It is to be understood that the instant disclosure is provided examparily to facilitate comprehension of the invention and should not be construed to limit the scope thereof.

What is claimed is:

1. A medical method, comprising:
   providing a hand-carried ultrasonic probe having transmission and reception capabilities;
   moving said probe by hand over a skin surface of a patient along an at least partially random path;
   during the moving of said probe, transmitting an outgoing ultrasonic pressure wave from said probe into the patient;
   also during the moving of said probe, receiving reflected ultrasonic pressure waves from internal tissues of the patient;
   periodically preprocessing the received reflected ultrasonic pressure waves to derive preliminary structural data pertaining to the internal tissues of the patient, said data consisting essentially of separate sets of data, each of said sets of data corresponding to a respective location of said probe relative to the patient;
   storing said sets of data;
   analyzing said preliminary structural data of the stored sets of data to determine three-dimensional shapes of the internal tissues of the patient; and
   generating a video signal encoding a relatively high-resolution video image of said three-dimensional shapes.

2. The method defined in claim 1 wherein the storing of said sets of data and the analyzing of said preliminary structural data occur automatically.

3. The method defined in claim 1 wherein said sets of data encode respective ultrasound images of the patient's internal tissues, the periodic analyzing of the received reflected ultrasonic pressure waves including generating said ultrasound images, each of said images being generated from a respective set of reflected ultrasonic pressure waves received immediately prior to generation of the respective ultrasound image.

4. The method defined in claim 1, further comprising transmitting said video signal to a video monitor and operating said monitor pursuant to said video signal to display said video image on said monitor, said video image having definition and quality approximating an image generated by an optical camera.

5. The method defined in claim 1 wherein said probe includes a carrier in the form of a wand having a handle portion and a head portion, the moving of said probe including holding said wand by said handle and moving said wand while maintaining said head in contact with the skin of the patient.

6. The method defined in claim 1 wherein said probe includes a plurality of acoustoelectric sensors, the receiving of the reflected ultrasonic pressure waves from the internal tissues of the patient including operating said sensors to generate respective electrical signals encoding said ultrasonic pressure waves.

7. The method defined in claim 1 wherein said probe includes a flat carrier and a plurality of acoustoelectric sensors, the receiving of the reflected ultrasonic pressure waves from the internal tissues of the patient including operating said sensors to generate respective electrical signals encoding said ultrasonic pressure waves.

8. The method defined in claim 1 wherein the analyzing of said preliminary structural data includes utilizing pattern recognition to identify three-dimensional shapes of known types.

9. A medical apparatus, comprising:
   a hand-carried ultrasonic probe having an ultrasonic wave emitter and an ultrasonic wave sensor, said probe being manually movable along an at least partially random path on a skin surface of a patient in pressure-wave transmitting contact with said skin surface;
   an ultrasonic frequency generator operatively connected to said wave emitter;
   an ultrasonic-wave preprocessor operatively connected to said sensor for periodically processing reflected ultrasonic pressure waves detected by said sensor to derive preliminary structural data pertaining to the internal tissues of the patient, said data consisting essentially of separate sets of data, each of said sets of data corresponding to a respective location of said probe relative to the patient;
   a memory operatively connected to said preprocessor for storing said sets of data; and
   a main processor operatively connected to at least one of said memory and said preprocessor for analyzing said preliminary structural data of the stored sets of data to determine three-dimensional shapes of the internal tissues of the patient and for generating a video signal encoding a relatively high-resolution video image of said three-dimensional shapes.

10. The apparatus defined in claim 9 wherein said preprocessor includes means for generating electrically encoded ultrasound images corresponding to said sets of data are, each of said images being generated from a respective set of reflected ultrasonic pressure waves received immediately prior to generation of the respective ultrasound image.

11. The apparatus defined in claim 9, further comprising a video monitor operatively connected to said main processor for receiving said video signal therefrom and displaying said video image, said video image having definition and quality approximating an image generated by an optical camera.

12. The apparatus defined in claim 9 wherein said probe includes a carrier in the form of a wand having a handle portion and a head portion.

13. The apparatus defined in claim 9 wherein said probe includes a plurality of acoustoelectric sensors operatively connected to said preprocessor.

14. The apparatus defined in claim 9 wherein said probe includes a flat carrier and a plurality of acoustoelectric sensors.

15. A medical apparatus, comprising:
   a hand-carried ultrasonic probe having an electroacoustic transducer and an acoustoelectric transducer;
   means connected to said probe for enabling manual movement of said probe by a user along an at least partially random path over a skin surface of a patient;

an ultrasonic signal generator operatively connected to said electroacoustic transducer for energizing said electroacoustic transducer to transmit an outgoing ultrasonic pressure wave into the patient;

a wave preprocessor operatively connected to said acoustoelectric transducer for analyzing the received reflected ultrasonic pressure waves detected by said acoustoelectric transducer and for deriving, from the received reflected ultrasonic pressure waves, preliminary structural data pertaining to the internal tissues of the patient, said data consisting essentially of separate sets of data, each of said sets of data corresponding to a respective location of said probe relative to the patient;

a memory operatively connected to said wave preprocessor for storing said sets of data;

a main processor operatively connected to said memory for analyzing said preliminary structural data of the stored sets of data to determine three-dimensional shapes of the internal tissues of the patient; and a video signal generator operatively connected to said main processor for encoding a relatively high-resolution video image of said three-dimensional shapes.

16. The apparatus defined in claim 15 wherein said means for enabling movement of said probe include a handle manipulable by an operator.

17. The apparatus defined in claim 15, further comprising a video monitor operatively connected to said video signal generator for receiving said video signal therefrom and displaying said video image.

18. The apparatus defined in claim 15 wherein said probe includes a carrier in the form of a wand having a handle portion and a head portion.

19. The apparatus defined in claim 15 wherein said memory is operatively connected to said wave preprocessor for automatically storing said sets of data in the absence of commands from an operator.

20. A medical method, comprising:

manually moving a hand-carried probe along an at least partially random path over a skin surface of a patient;

during the moving of said probe, transmitting an outgoing ultrasonic pressure wave from said probe into the patient;

receiving reflected ultrasonic pressure waves from internal tissues of the patient;

processing the received reflected ultrasonic pressure waves to determine three-dimensional shapes of the internal tissues of the patient; and generating a video signal encoding a relatively high-resolution video image of said three-dimensional shapes, wherein the processing of the reflected ultrasonic pressure waves includes executing pattern recognition processes to compare partial tissue structures with stored structural tissue data to identify tissue structures.

* * * * *